United States Patent [19]

Chandra et al.

[11] Patent Number: 4,788,313
[45] Date of Patent: Nov. 29, 1988

[54] SILALACTONES AND METHODS FOR THEIR PREPARATION AND USE

[75] Inventors: Grish Chandra; Donnie R. Juen, both of Midland, Mich.

[73] Assignee: Dow Corning Corporation, Midland, Mich.

[21] Appl. No.: 565,075

[22] Filed: Dec. 23, 1983

[51] Int. Cl.$^4$ .............................. C07F 7/08; C07F 7/18
[52] U.S. Cl. .................................................. 556/442
[58] Field of Search ........................................ 556/442

[56] References Cited

U.S. PATENT DOCUMENTS

| | | | |
|---|---|---|---|
| 2,449,987 | 9/1948 | Gresham | 556/442 X |
| 2,589,446 | 4/1950 | Sommer | 260/448.2 |
| 2,635,109 | 10/1951 | Sommer | 260/448.2 |
| 2,963,500 | 12/1960 | Sommer | 260/448.2 |
| 3,395,167 | 7/1968 | Saam | 260/448.2 |
| 4,392,483 | 5/1982 | Speier | 556/436 |

*Primary Examiner*—Paul F. Shaver
*Attorney, Agent, or Firm*—George A. Grindahl

[57] ABSTRACT

Carboxyalkyl-substituted organopolysiloxanes are prepared by hydrolysis of a silalactone composition having the formula

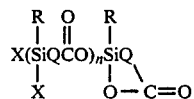

where n has an average value greater than zero, R and Q are hydrocarbon and X is Cl or Br. Silicon-containing compounds having the formula $R_aZ_bSiO_{(4-a-b)/2}$, where Z is a hydrolyzable radical, can be cohydrolyzed therewith. The novel silalactone composition is prepared by gently heating a mixture of an ester having the formula $X_2R\,SiQCO_2R'$ and a halide salt catalyst, such as tetrabutylammonium bromide.

14 Claims, No Drawings

SILALACTONES AND METHODS FOR THEIR PREPARATION AND USE

BACKGROUND OF THE INVENTION

The present invention relates to silalactones, to a method for their preparation and to methods for preparing carboxyalkyl-substituted organopolysiloxanes therefrom.

Carboxyalkyl-substituted organopolysiloxanes are known from U.S. Pat. Nos. 2,723,987; 2,900,363; 3,119,855 and 3,391,177 and their utility as metal protectants and paper sizings is known from U.S. Pat. Nos. 3,755,071 and 4,011,362.

The methods disclosed in the art for the preparation of carboxyalkyl-substituted organopolysiloxanes typically comprise a hydrolysis reaction of a cyanolkyl-substituted hydrolyzable silane or a carbalkoxyalkyl-substituted hydrolyzable silane to prepare the carboxyalkyl-substituted siloxane unit, followed by a silanol condensation reaction and/or a siloxane equilibration reaction to provide the desired carboxyalkyl-substituted siloxane.

However, these methods for preparing carboxyalkyl-substituted organopolysiloxanes are not completely satisfactory in-as-much as the hydrolysis reaction of said cyano- or carbalkoxy-alkyl substituent is rarely complete and the final organopolysiloxane contains various amounts of residual radicals, such as cyanoalkyl radicals or carbalkoxyalkyl radicals. A method for preparing carboxyalkyl-substituted organopolysiloxanes which are free of such residual radicals is desired.

Silalactones are known from U.S. Pat. Nos. 2,589,446; 2,635,109; 2,963,500 and 3,395,167; however, the silalactones disclosed therein contain, or give rise to, triorganosiloxy units and are therefore not useful for preparing organopolysiloxanes which contain more than two carboxyalkly substituents per molecule. Although the above-noted silalactone patents disclose that the triorganosiloxy-containing silalactones described therein are useful for preparing disiloxane dicarboxylic acids and various organofunctional organosiloxanes, no further teachings relative to carboxyalkyl-substituted organopolysiloxanes are given. Examples of said triorganosiloxy-containing or -forming silalactones of the art include

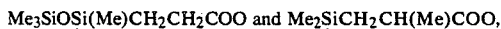
Me₃SiOSi(Me)CH₂CH₂COO and Me₂SiCH₂CH(Me)COO, wherein Me denotes the methyl radical.

U.S. Pat. No. 3,395,167 further discloses a process for preparing the triorganosiloxy-containing silalactone. Said process comprises heating an ester having the formula $XR_2Si(CR_2')_nCOOA$. The use of a halide salt catalyst to aid the reaction or the use of an ester containing two silicon-bonded X atoms was not contemplated in said patent.

U.S. Pat. No. 4,329,483 discloses a process for preparing a cyclotetrasiloxane and either an acyl chloride or an aliphatic chloride. Said process comprises sufficiently heating a reaction mass comprising an ester group and at least one ≡SiCl group until the cyclotetrasiloxane is formed. Halide salt catalysts were said to aid the reaction. Although some of the reaction mixtures that are used in the method of the present invention were disclosed as a suitable reaction mass, the preparation of silalactones was not disclosed.

BRIEF SUMMARY OF THE INVENTION

It is an object of this invention to provide a method for the preparation of carboxyalkyl-substituted organopolysiloxanes which are substantially free of undesired silicon-bonded residual radicals. It is a further object of this invention to provide silalactone compositions which are useful for preparing carboxyalkyl-substituted organopolysiloxanes. It is also an object of this invention to provide a method for preparing novel silalactone compositions. It is yet another object of the present invention to provide a one-pot method for the preparation of carboxyalkyl-substituted organopolysiloxanes from carbalkoxyalkyl-substituted organodihalosilanes.

These objects, and others which will become apparent upon consideration of the following disclosure and claims, are obtained by this invention which, briefly stated, comprises gently heating a compound of the formula $RX_2SiQCO_2R'$ in the presence of a halide salt catalyst to provide a silalactone composition having the average formula

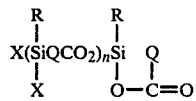

$$\begin{array}{ccc} & R & R \\ & | & | \\ X(SiQCO_2)_n & Si & Q \\ & | & | \; | \\ & X & O-C=O \end{array}$$

and then hydrolyzing the resulting silalactone composition, optionally, in the presence of other silicon-containing materials to provide an organopolysiloxane containing one or more siloxane units having the formula

$$\begin{array}{c} RSiO_{2/2} \\ | \\ QCOOH \end{array}$$

In accordance with one of the objects of this invention, carboxyalkyl-substituted organopolysiloxanes free of residual radicals are produced by the process of this invention because the silalactone composition readily hydrolyzes and enters the siloxane structure as a carboxyalkly-substituted silicon atom.

DETAILED DESCRIPTION OF THE INVENTION

The above, briefly described, invention will now be fully delineated in all its aspects.

In a first aspect, the present invention relates to a silalactone composition having the formula

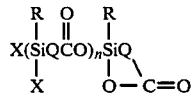

$$\begin{array}{ccc} & R & O & R \\ & | & \| & | \\ X(SiQCO)_n & Si Q \\ & | & | \; \backslash \\ & X & O-C=O \end{array}$$

wherein X denotes a chlorine or bromine atom, R denotes a monovalent hydrocarbon radical, Q denotes a divalent hydrocarbon radical, there being at least two carbon atoms in Q separating a silicon atom and a carbonyl carbon atom, and n has an average value greater than zero.

In a second aspect, the present invention relates to a method comprising heating, under substantially anhydrous conditions, a reaction mixture comprising a halide salt catalyst selected from the group consisting of quaternary ammonium halide salts, quaternary phosphonium halide salts and alkyl pyridinium halide salts and an ester having the formula X₂RSiQCOOR' wherein X denotes a chlorine or bromine atom, R denotes a monovalent hydrocarbon radical, Q denotes a divalent hydrocarbon radical, there being at least two carbon atoms in Q separating a silicon atom and carbonyl carbon atom, and R' denotes an alkyl radical, said heating being sufficient to produce a silalactone composition having the formula

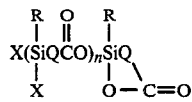

wherein X, R and Q have the meanings recited above and n has an average value greater than zero.

In a third aspect, the present invention relates to a method comprising mixing the silalactone composition of the second aspect of this invention with water in sufficient amount to hydrolyze substantially all hydrolyzable bonds attached to silicon in the silalactone composition and to provide an organopolysiloxane containing one or more siloxane units having the formula

wherein R and Q have the stated meanings.

In a fourth aspect, the present invention relates to a method comprising mixing a silalactone composition having the formula

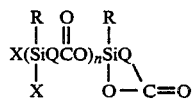

and a sufficient amount of water to provide an organopolysiloxane containing one or more siloxane units having the formula

wherein, at each occurrence, X denotes a chlorine or bromine atom, R denotes a monovalent hydrocarbon radical, Q denotes a divalent hydrocarbon radical, there being at least two carbon atoms in Q separating a silicon atom and a carbonyl carbon atom, and n has an average value of greater than aero, said amount of water being sufficient to hydrolyze substantially all hydrolyzable bonds attached to silicon in the silalactone composition.

The silalactone compositions of this invention have the formula

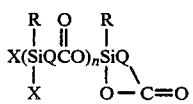

wherein n has an average value greater than zero, such as 0.5, 1.0, 3.0, 4.5, 7.7, 10 and more. It is to be noted that the silalactone compositions of the present invention comprise a mixture of silalactones wherein n has a value of 0, 1, 2, 3, 4, 5, 6, 7, 8, 9, 10 or more for any particular member, the exact members of the mixture being dependent on many factors such as the nature of Q, R, X, etc. Thus, although the silalactone compositions of this invention contain monomeric silalactones (n=0), which can be separated therefrom, they are, on average, polymeric silalactones (n>0).

The silalactone compositions of this invention contain about one silicon-bonded X atom per silicon atom, where X denotes a chlorine or bromine atom. It is thought that silalactone compositions of the above formula wherein X denotes a fluorine atom or an iodine atom, although having utility for the preparing of carboxyalkyl-substituted organopolysiloxanes, are not as cleanly produced by the method of this invention as are the silalactone compositions of this invention where X is a chlorine atom or a bromine atom. That is to say, when X is a chlorine atom or a bromine atom the silalactone compositions of this invention are produced substantially freer of other products by the method of this invention than when X is fluorine or iodine. Preferably X denotes a chlorine atom rather than a bromine atom for the same types of reasons but to a lesser extent.

The silalactone compositions of this invention contain about one silicon-bonded R radical per silicon atom, said R radical being a monovalent hydrocarbon radical. Examples of suitable R radicals include alkyl radicals, such as methyl, ethyl, propyl, isopropyl, n-butyl, s-butyl, t-butyl, hexyl and decyl; alkenyl radicals, such as vinyl and allyl; cycloaliphatic radicals, such as cyclohexyl; and aryl radicals, such as phenyl, benzyl and tolyl. Preferably R contains from 1 to 6 carbon atoms. Most preferably R is the methyl radical.

The silalactone compositions of the present invention contain one silicon-bonded Q radical per silicon atom, wherein Q denotes a divalent hydrocarbon radical linking a silicon atom and a carbonyl carbon atom. There must be at least two carbon atoms in Q which separate the silicon atom from the carbonyl carbon atoms, thereby permitting the formation of a silalactone. Examples of suitable Q radicals include alkylene radicals such as —CH₂CH₂—,

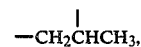

—CH₂CH₂CH₂—, —CH₂CH(CH₃)CH₂—, —(CH₂)₅—, —(CH₂)₆—, and —(CH₂)₈—and arylene radicals such as —CH₂CH₂C₆H₄CH₂—. Preferably Q contains from 2 to 5 carbon atoms. In view of the typical method for synthesizing the ester precursor of the silalactone compositions of this invention, detailed below, Q preferably has a —CH₂ portion thereof bonded to the silicon atom.

A highly preferred silalactone composition of this invention has the formula

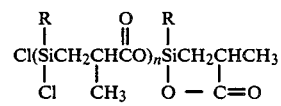

where R has the general and preferred meaning denoted above, most preferably —CH₃.

Other examples of preferred silalactone compositions of this invention include the following where Ph denotes phenyl.

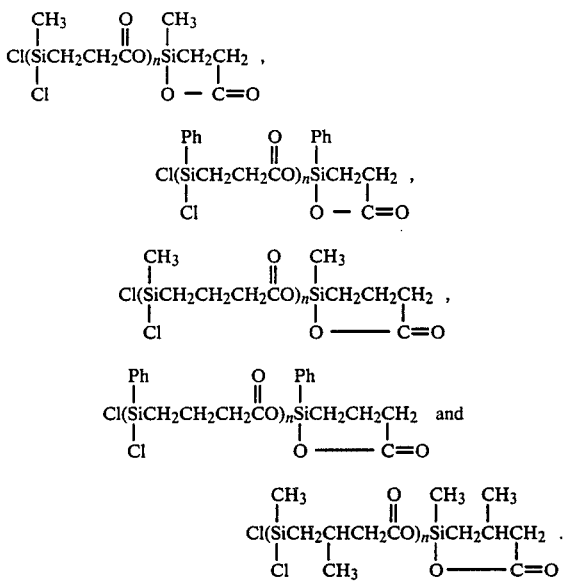

The silalactone compositions of this invention are, at the present time, most accurately characterized by spectroscopic means as illustrated by the examples disclosed below. However, they are also further characterized by chemical reactions, such as conversion by hydrolysis to carboxyalky-substituted siloxane units having the formula

The silalactone compositions of this invention are to the best of the inventors' knowledge, produced solely by the method of this invention, noted above and further delineated below. In said method an ester having the formula $X_2RSiQCO_2R'$ is gently heated in the presence of a halide salt catalyst and in the absence of liquid or gaseous water, whereupon the silalactone composition of this invention and an alkyl halide having the formula R'X are coproduced.

In the above formula for the ester X, R and Q have the general and preferred meanings delineated above for the silalactone compositions of this invention and R' denotes an alkyl radical, preferably a lower alkyl radical having from 1 to 6 carbon atoms, and most preferably the methyl radical.

Examples of esters which provide preferred silalactone compositions of this invention when used in the method of this invention include the following: $Cl_2CH_3SiCH_2CHCH_3CO_2CH_3$, $Cl_2CH_3SiCH_2CHCH_3CO_2CH_2CH_3$, $Cl_2CH_3SiCH_2CH_2CO_2CH_3$, $Cl_2CH_3SiCH_2CH_2CO_2CH_2CH_2$, $Cl_2CH_3SiCH_2CHCH_3CH_2CO_2CH_3$, $Cl_2CH_3SICH_2CHCH_3CH_2CO_2CH$ $_2CH_3$, $Cl_2CH_3Si(CH_2)_3CO_2CH_3$, $Cl_2CH_3Si(CH_2)_3CO_2CH_2CH_3$, $Cl_2PhSiCH_2CHCH_3CO_2CH_3$, $Cl_2PhSi(CH_2)_3CO_2CH_3$, $Cl_2PhSi(CH_2)_2CO_2CH_3$ and $Cl_2PhSiCH_2CHCH_3CH_2CO_2CH_3$.

Esters having the formula $X_2RSiCH_2CHQ'CO_2R'$ are typically prepared by a hyrosilylation reaction between a silane having the formula $X_2RSiH$ and an ester having the formula $CH_2=CQ'CO_2R'$ wherein Q' denotes the residue obtained when the unit $-CH_2-CH$ is removed from Q. For example, when Q denotes $-CH_2CH_2-$, Q' denotes H and when Q denotes

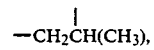

Q' denotes $CH_3$. The disclosure of U.S. Pat. No. 2,823,218 is incorporated herein by reference to teach a preferred hydrosilylation reaction and its use to prepare esters, including preferred esters that are used in the method of this invention.

By gently heated it is meant herein that the mixture of ester and halide salts catalyst is heated sufficiently, with respect to temperature and duration of heating, to prepare the silalactone composition of this invention but not so vigorously as to produce more than trace amounts of other products such as organosiloxanes, carboxylic anhydrides and acyl chlorides.

Typically the mixture of ester and halide salt catalyst is heated for 0.5 to 2 hours at a room temperature of from 50° to 150° C., preferably 110° C. to 140° C. Heating temperatures substantially higher than 150° C. and reaction times, i.e. time when reaction is occurring, substantially longer than 2 hours produce undesirable products in that non-silalactone products are formed. Frequently the non-silalactone products that are produced by higher temperatures and/or longer reaction times are useful as precursors for the preparation of carboxyalkyl-substituted organopolysiloxanes; however, the product is an undesirable product because it is difficult to handle, especially on a commercial scale. In the absence of any benefit for doing otherwise one should not heat the mixture of ester and halide salt catalyst for more than 2 hours at 150° C.

The halide salt catalyst that is used in the method of this invention is selected from the group consisting of quaternary ammonium halide salts, quaternary phosphonium halide salts and alkyl pyridinium halide salts. The halide portion includes iodides, bromides and chlorides. Examples of said halide salt catalysts, where Bu denotes the n-butyl radical, include $Bu_4N^+Br^-$, $Bu_4N^+Cl^-$, $Bu_4N^+I^-$, $C_{C5}H_5N^+(CH_3)Br^-$, $C_5H_5N^+(CH_3)I^-$, $C_5H_5N^+(CH_2CH_3)Br^-$, $C_5H_5N^+(CH_2$those alkyl pyridinium halide salts disclosed by Mahone, U.S. Pat. No. 4,108,882.

The amount of halide salt catalyst to be mixed with the ester in the method of this invention is not critical as long as there is a sufficient amount of allow the preparation of the silalactone composition of this invention with gentle heating. Typically from 0.1 to 10, preferably 1 to 5 percent by weight, based on the weight of ester plus halide salt catalyst, of halide salt is used.

Although not being required a liquid diluent for the mixture of ester and halide salt catalyst can be used, if desired. Preferably said diluent is an inert liquid such as toluene or xylene.

In the method of this invention the mixture of ester and halide salt catalyst can be heated at any pressure, such as at subatmospheric, atmospheric or superatmospheric pressure and in either an open or a closed system. Preferably said heating is done in such a manner than any reaction product, such as R'X, that is co-produced with the silalactone composition and which is volatile at the heating temperature is removed from the reaction zone as it is formed. In the preferred embodiment of this invention, R'X denotes $CH_3Cl$ which readily, and substantially quantitatively, exits the reaction zone when the method is performed at atmospheric pressure in an open system; leaving the silalactone composition of this invention in the reaction zone.

The silalactone compositions of this invention are useful as a precursor material for the preparation of carboxyalkly-substituted siloxane polymers and copolymers.

Thus, the present invention further relates to a method for preparing an organopolysiloxane which contains one or more siloxane units having the formula

Said method comprises, in its broadest aspect, mixing a composition comprising a silalactone composition having the formula

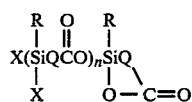

with water in sufficient amount to convert substantially all of the silalactone compositions to

siloxane units.

The silalactone composition that is mixed with water in the method of this invention can be the general or preferred silalactone compositions that are produced by the method of this invention, hereinabove delineated, or the general or preferred silalactone composition of this invention hereinabove delineated, that are produced by any other suitable method. In particular the silalactone compositions that have been produced by the method of this invention can be directly converted to an organopolysiloxane without further purification.

When the silalactone composition contains no other silicon-containing components the mixing of a sufficient amount of water therewith according to the method of this invention provides a homopolymeric organopolysiloxane having the formula

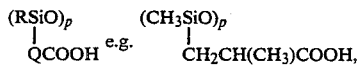

which represents cyclic and/or silanol-terminated linear organopolysiloxanes wherein p has an average value of 2 or more.

The silalactone composition to be hydrolyzed can further contain a silicon-containing component having the formula

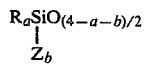

in which case linear and/or cyclic copolymeric organopolysiloxanes containing one or more

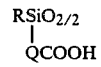

siloxane units and one or more $R_aSiO_{(4-a)/2}$ siloxane units are obtained by the method of this invention. The linear copolymeric organopolysiloxanes can be silanol-terminated or organo-terminated, depending on the value of a.

Alternatively, the silicon-containing component having the formula

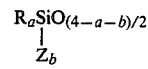

can be added to the hydrolyzed silalactone composition and, if needed, additional water added thereto to hydrolyze any Z radicals that are present. A linear and/or cyclic copolymeric organopolysiloxane is likewise obtained therefrom.

The homopolymeric or copolymeric organopolysiloxane can, optionally, be further condensed and/or equilibrated preferaby under acid catalysts, to provide improved organopolysiloxanes with respect to the ratio of linear/cyclic siloxanes in the well-known manner. Residual acid is thereafter preferably neutralized by well-known methods.

In the above formula for the silicon-containing component R has the general and preferred meanings noted above for the silalactone compositions of this invention and Z denotes a hydrolyzable radical. Examples of suitable Z radicals include halogen atoms, such as chlorine and bromine; alkoxy radicals, such as methoxy, ethoxy and propoxy; amino and substituted amino radicals such as $-NH_2$, $-NHR$ and $-NHSiR_3$; and acyloxy radicals, such as acetoxy.

Examples of silicon-containing compounds having the formula

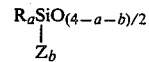

include halosilanes, such as $R_3SiCl$, such as $(CH_3)_3SiCl$, $(CH_3)_2(CH_2=CH)SiCl$ and $(Ph)(CH_3)(CH_2=CH)SiCl$; $R_2SiCl_2$, such as $(CH_3)_2SiCl_2$, $(Ph)(CH_3)SiCl_2$ and $(CH_3)(CH_2=CH)SiCl_2$; $RSiCl_3$, such as $CH_3SiCl_3$, $(CH_2=CH)SiCl_3$ and $PhSiCl_3$; and $SiCl_4$: disiloxanes, such as $(R_3Si)_2O$, such as $(CH_3)_3SiOSi(CH_3)_3$ and $(Ph)(CH_3)(CH_2=CH)SiOSi(CH_2=CH)(CH_3)(Ph)$ and polysiloxanes, such as $(R_2SiO)_q$, such as $((CH_3)_2SiO)_q$ and $((CH_3)(CH_2=CH)SiO)_q$ where q is 3, 4, 5, 6 and more; and $R_3)SiO(R_2SiO)_xSiR_3$, such as $(CH_3)_3SiO((CH_3_2S$ x has a value of 1 or more. The values of a and b range from 0 to 3 and 0 to 4, respectively, with the total of a+b having a value of from 1 to 4.

The water that is used in the method of this invention can optionally contain one or more additives, such as acids, buffers, solvents and surfactants.

In the method of this invention the mixing of the water and the silalactone composition can be conducted at any suitable temperature. For example, the mixing can be conducted at autogenous temperatures or heat can be added to or removed from the reaction mixture, as desired. Subsequent condensation and/or equilibration of the hydrolyzed composition is preferably conducted at elevated temperature, such as 50° to 150° C., preferably at 80° to 130° C., in the well-known manner. Neutralization of any residual acid is preferably conducted at lower temperatures, such as room temperature.

The present invention is particularly useful for preparing organo-terminated organopolysiloxanes having the formula

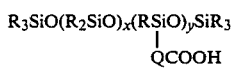

wherein R and Q have the meanings noted above, including the preferred embodiments thereof. The value of x can be 0 or more and the value of y can be 1 or more.

For example, a silalactone composition of this invention can be mixed with a disiloxane having the formula $R_3SiOSiR_3$ and the mixture hydrolyzed and equilibrated under acid conditions to provide an organopolysiloxane having the formula

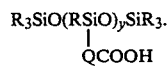

Alternatively, $R_3SiCl$ can be used with, or in place of, the $R_3SiOSiR_3$.

For another example, a silalactone composition of this invention can be mixed with water to provide a mixture of cyclic and silanol-terminated linear organopolysiloxane having the formula

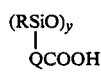

which can be mixed with $R_3SiO(R_2SiO)_xSiR_3$ and the mixture equilibrated to provide an organopolysiloxane having the formula

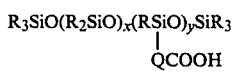

wherein the values of x and y are greater than 1. Alternatively, a mixture of $R_3SiCl$ and $R_2SiCl_2$ can be used in place of $R_3SiO(R_2SiO)_xSiR_3$.

In like manner, any of the carboxyalkyl-substituted organopolysiloxanes of the art having the formula

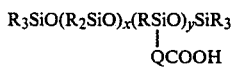

can be prepared by the method of this invention.

The following examples are disclosed to further teach how to practice, but not to limit, the present invention which is properly delineated by the appended claims. All parts and percentages are by weight unless otherwise stated. Herein, Me denotes the methyl radical, Bu denotes the n-butyl radical, Et denotes the ethyl radical.

EXAMPLE 1

This example illustrates the preparation of a silalactone composition of this invention by a method of this invention.

A mixture of 100.2 parts of $MeCl_2SiCH_2CH(Me)CO_2Me$ and 2.16 parts of $Bu_4N^+Br^-$ was heated under anhydrous conditions for 2 hours at 128° to 150° C. MeCl, 20.57 parts and MeBr, 0.4 parts were evolved. A viscous liquid, 78.6 parts, remained in the reaction vessel.

The viscous liquid was analyzed with $^1H$ nuclear magnetic resonance (n.m.r.) and infrared (i.r.) spectroscopy. $^1H$ n.m.r.: $Cl_2SiCH_3)CH_2$—, 0.84 ppm; OCl-Si(CH_3)CH_2—, 0.65 ppm;

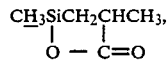

0.55 ppm;

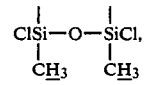

0.36 ppm (small amount); 1.r.: $-CO_2Si$ (linear), 1735 cm$^{-1}$; $-CO_2Si$ (lactone), 1780 cm$^1$; —COCl, 1815 cm$^{-1}$ and 1785 cm$^{-1}$ (small amount); SiCl, 535 cm$^{-1}$ and 475 cm$^{-1}$.

EXAMPLE 2

This example illustrates the preparation of an organopolysiloxane by the method of this invention.

A portion, (7.31 parts), of the silalactone composition produced in Example 1 was mixed with 0.84 parts of $H_2O$ and 8.0 parts of $Et_2O$. The mixture was stirred at room temperature for 4 hours, after which 0.87 parts of $H_2O$ were added and the stirring was continued. The resulting hydrolyzed silalactone was dried and devolatilized at 80° C. and 1 mm of Hg pressure to provide 3.47 parts of a waxy material having the unit formula

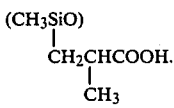

The waxy material was analyzed by nuclear magnetic resonance using $^1H$, $^{29}Si$ and $^{13}C$ nuclei. Si—$CH_3$ (0.17 ppm, singlet, 3H); Si—$CH_2$ (0.4 to 1.1 ppm, multiplet, 2H); C$\underline{H}$CH$_3$ (2.6 ppm, quartet, 1H); —CHC$\underline{H}_3$ (1.2 ppm, doublet, 3H); —COOH(11.4 ppm, singlet, 1H): SiO cyclic (-20.58 ppm); SiO linear (−22.92 ppm): SiCH$_3$ (-1.01 ppm); SiCH$_2$ (20.84 ppm); CHCH$_3$ (33.49 ppm); CHCH$_3$ (18.90 ppm); —COOH (179.08 ppm).

EXAMPLE 3

This example illustrates the preparation of a copolymeric siloxane by the method of this invention.

Example 1 was repeated and 39.48 parts of the resulting silalactone composition was mixed with 4.53 parts of $H_2O$, 153.08 parts of cyclodimethylsiloxane and 7.44 parts of $Me_3SiO(Me_2SiO)_2SiMe_3$ and the mixture was stirred at 80° C. for about 1 hour. An equilibration catalyst (0.2 parts of $CF_3SO_3H$) was added to the heated mixture and the mixture was allowed to equilibrate until the viscosity became constant (4 hours). The fluid was cooled, the catalyst and residual HCl neutralized with NaHCO$_3$, dried and filtered to provide a fluid having the formula

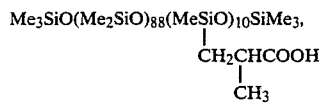

a viscosity of 1800 centistokes (0.0018 m2/s) at 25° C., 0.14% Na+ and 5.41% —COOH by titration, (theory 5.53%).

EXAMPLE 4

A mixture of $MeCl_2SiCH_2CH(Me)CO_2Me$, 98 parts, and $Bu_4N^+Br^-$, 2 parts, was prepared and a small portion thereof was sealed into each of four glass tubes. The sealed tubes were exposed to four different combinations of temperature and time and were thereafter opened at low temperature, the volatile products were allowed to escape at room temperature and the material remaining in the tube was analyzed by infrared spectroscopy. The results, summarized in the Table, show that when gentle heating is used the starting mixture provides a silalactone composition of this invention. However, when a longer heating period (24 hours) and/or a higher temperature (200° C.) is used, by products such as siloxanes and acyl chlorides are formed.

The product that was obtained at 150° C./1.5 hr. was also analyzed by 1H n.m.r. The integration of protons in methyl groups bonded to the three types of silicon atoms that are present in

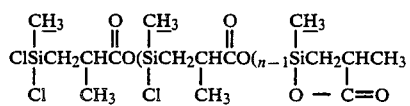

shows that n had a value of about 3.

TABLE

| Conditions | Infrared Absorptions*, cm$^{-1}$ | | | | | |
|---|---|---|---|---|---|---|
| | —CO$_2$Me | —CO$_2$Si— | —SiQCOO | —SiCl | —SiOSi— | —COCl |
| Starting ester | 1740(s) | — | — | 535(s) to (m) 475(m) | — | — |
| 150° C./1.5 hour | — | 1740(vs) | 1780(vs) | 535(m) 475(w) to (m) | — | — |
| 150° C./24 hours | — | 1740(vs) | 1780(s) | 535(ms) 475(mw) | 1100(vs,br) | 1785(s) 1820(m) |
| 200° C./1 hour | Very similar to 150°/24 hour product | | | | | |
| 200° C./24 hours | — | 1740(vs) | 1780(s) | 535(vw) 475(vw) | 1100(vs,br) | 1785(vs) 1820(m) |

*s = strong, w = weak, m = medium, v = very, br = broad

EXAMPLE 5

This examples illustrates, in a quantitative manner, the undesirable results of heating an ester for 24 hours instead of for 2 hours at 150° C.

A mixture of $MeCl_2SiCH_2CH(Me)CO_2Me$, 30 parts and $Bu_4N^+Br^-$, 0.6 parts was heated at 150° C. for 24 hours and the MeCl was allowed to exit the reaction flask and was collected in a cold trap. The material remaining in the flask was mixed with 8.9 parts of MeOH, 28.2 parts of Et$_3$N and pentane to convert ≡SiCl to ≡SiOMe, —COCl to —CO$_2$Me and —CO$_2$Si≡ to —CO$_2$H and SiOMe. Infrared and nuclear magnetic resonance spectroscopy performed on the resulting products of methanolysis showed that about 40 to 45 percent of the carbonyl groups were present as —COCl groups and 55 to 60 percent as —COOSi≡ groups. When the reaction was repeated at 150°C. for 2 hours, 10 to 15 percent of the carbonyl groups were present as —COCl groups and 85 to 90% as —COOSi≡ groups.

EXAMPLE 6

Example 1 was repeated on a larger scale. At room temperature the halide salt catalyst was noted to be floating on the surface of the ester; however, at 60° C. the mixture had become homogeneous and MeCl was being evolved and was being collected in a cold trap. The temperature of the mixture was gradually raised from room temperature to 120° C. over a period of 93 minutes and then to 132° C. over a period of 24 minutes where it was kept for an additional 88 minutes. A major portion of the MeCl was evolved at temperature of 120° C. or less. The product was sampled at 90 minutes, 117 minutes and at 205 minutes and analyzed by $^1$H n.m.r. spectroscopy. The ester was 57.1% reacted after 93 minutes, 76.4% after 117 minutes and almost completely reacted after 205 minutes.

That which is claimed is:

1. A method comprising heating, under substantially anhydrous conditions, a reaction mixture comprising a halide salt catalyst selected from the group consisting of quaternary ammonium halide salts, quaternary phosphonium halide salts and alkyl pyridinium halide salts and an ester having the formula $X_2RSiQCOOR'$ wherein X denotes a chlorine or bromine atom, R denotes a monovalent hydrocarbon radical, Q denotes a divalent hydrocarbon radical, there being at least two carbon atoms in Q separating a silicon atom and a carbonyl carbon atom, and R' denotes an alkyl radical, said heating being sufficient to produce a silalactone composition having the formula

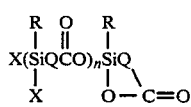

wherein X, R and Q have the meanings recited above and n has an average value greater than zero and further comprising mixing water with the silalactone composition in sufficient amount to hydrolyze substantially all hydrolyzable bonds attached to silicon in the silalactone composition and to provide an organopolysiloxane containing one or more siloxane units having the formula $$\underset{\underset{\text{QCOOH}}{|}}{\text{RSiO}_{2/2}}$$

wherein R and Q have the stated meanings.

2. A method according to claim 1 wherein X denotes a chlorine atom.

3. A method according to claim 2 further comprising mixing with the silalactone composition or the hydrolyzed silalactone composition a silicon-containing compound having the unit formula $$\underset{\underset{Z_b}{|}}{R_a\text{SiO}_{(4-a-b)/2}}$$

wherein R is as recited above, Z denotes a hydrolyzable radical, a has an average value of from 0 to 3, b has an average value of from 0 to 4 and a+b has an average value of from 1 to 4 to provide an organopolysiloxane containing one or more siloxane units having the formula $$\underset{\underset{\text{QCOOH}}{|}}{\text{RSiO}_{2/2}}$$

and one or more siloxane units having the formula $R_a\text{Si}O_{(4-a)/2}$ wherein a, R and Q have the stated meanings.

4. A method according to claim 3 wherein the organopolysiloxane has the formula $$\underset{\underset{\text{QCOOH}}{|}}{R_3\text{SiO}(R_2\text{SiO})_x(R\text{SiO})_y\text{SiR}_3}$$

wherein x has an average value of 0 or more, y has an average value of 1 or more and R and Q have the recited meanings.

5. A method according to claim 4 wherein Q contains from 2 to 5 carbon atoms and R and R' each contains from 1 to 6 carbon atoms.

6. A method according to claim 5 wherein Q denotes $$-\text{CH}_2\overset{|}{\text{CH}}\text{CH}_3,$$

the —CH$_2$ portion thereof being bonded to a silicon atom.

7. A method according to claim 6 wherein each R denotes —CH$_3$.

8. A method comprising mixing a silalactone composition having the formula $$\underset{\underset{X}{|}}{\overset{\overset{R}{|}}{X(\text{SiQCO})_n}}\underset{\underset{O-C=O}{|}}{\overset{\overset{O}{\|}}{\text{Si}}}\overset{R}{\underset{|}{Q}}$$

and a sufficient amount of water to provide an organopolysiloxane containing one or more siloxane units having the formula $$\underset{\underset{\text{QCOOH}}{|}}{\text{RSiO}_{2/2}}$$

wherein, at each occurrence, X denotes a chlorine or bromine atom, R denotes a monovalent hydrocarbon radical, Q denotes a divalent hydrocarbon radical, there being at least two carbon atoms in Q separating a silicon atom and a carbonyl carbon atom, and n has an average value greater than zero, said amount of water being sufficient to hydrolyze substantially all hydrolyzable bonds attached to silicon in the silalactone compositions.

9. A method according to claim 8 wherein X denotes a chlorine atom.

10. A method according to claim 9 further comprising mixing with the silalactone composition or the hydrolyzed silalactone composition a silicon-containing compound having the unit formula $$\underset{\underset{Z_b}{|}}{R_a\text{SiO}_{(4-a-b)/2}}$$

wherein R is as recited above, Z denotes a hydrolyzable radical, a has an average value of from 0 to 3, b has an average value of from 0 to 4 and a+b has an average value of from 1 to 4 to provide an organopolysiloxane containing one or more siloxane units having the formula $$\underset{\underset{\text{QCOOH}}{|}}{\text{RSiO}_{2/2}}$$

and one or more siloxane units having the formula $R_a\text{Si}O_{(4-a)/2}$ wherein a, R and Q have the stated meanings.

11. A method according to claim 10 wherein the organopolysiloxane has the formula $$\underset{\underset{\text{QCOOH}}{|}}{R_3\text{SiO}(R_2\text{SiO})_x(R\text{SiO})_y\text{SiR}_3}$$

wherein x has an average value of 0 or more, y has an average value of 1 or more and R and Q have the recited meanings.

12. A method according to claim 11 wherein Q contains from 2 to 5 carbon atoms and R and R' each contain from 1 to 6 carbon atoms.

13. A method according to claim 12 wherein Q denotes $$-\text{CH}_2\overset{|}{\text{CH}}\text{CH}_3,$$

the —CH$_2$ portion thereof being bonded to a silicon atom.

14. A method according to claim 13 wherein each R denotes —CH$_3$.

* * * * *